United States Patent
Govari et al.

(10) Patent No.: US 9,241,656 B2
(45) Date of Patent: Jan. 26, 2016

(54) SERIALLY CONNECTED AUTONOMOUS LOCATION PADS

(71) Applicant: BIOSENSE WEBSTER (ISRAEL) LTD., Yokneam (IL)

(72) Inventors: Assaf Govari, Haifa (IL); Yaron Ephrath, Karkur (IL); Andres Claudio Altmann, Haifa (IL)

(*) Notice: Subject to any disclaimer, the term of this patent is extended or adjusted under 35 U.S.C. 154(b) by 94 days.

(21) Appl. No.: 14/063,418

(22) Filed: Oct. 25, 2013

(65) Prior Publication Data

US 2015/0119686 A1 Apr. 30, 2015

(51) Int. Cl.
*A61B 5/06* (2006.01)
*G01B 7/004* (2006.01)

(52) U.S. Cl.
CPC .............. *A61B 5/062* (2013.01); *G01B 7/004* (2013.01)

(58) Field of Classification Search
CPC ...... A61B 5/04005; A61B 5/055; A61B 5/06; A61B 5/062
See application file for complete search history.

(56) References Cited

U.S. PATENT DOCUMENTS

| | | | |
|---|---|---|---|
| 5,211,165 A | 5/1993 | Dumoulin et al. |
| 5,391,199 A | 2/1995 | Ben-Haim |
| 5,443,489 A | 8/1995 | Ben-Haim |
| 5,558,091 A | 9/1996 | Acker |
| 6,172,499 B1 | 1/2001 | Ashe |
| 6,177,792 B1 | 1/2001 | Govari |
| 6,239,724 B1 | 5/2001 | Doron |
| 6,288,785 B1 | 9/2001 | Frantz |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben-Haim |
| 6,788,967 B2 | 9/2004 | Ben-Haim |
| 2001/0045826 A1 | 11/2001 | Schneider |
| 2002/0065455 A1 | 5/2002 | Ben-Haim et al. |
| 2003/0120150 A1 | 6/2003 | Govari |
| 2004/0068178 A1 | 4/2004 | Govari |
| 2006/0241397 A1 | 10/2006 | Govari et al. |
| 2011/0224537 A1 | 9/2011 | Brunner |

FOREIGN PATENT DOCUMENTS

| | | |
|---|---|---|
| EP | 0894473 A2 | 2/1999 |
| EP | 1202077 A2 | 5/2002 |
| WO | WO 96/05768 A1 | 2/1996 |

OTHER PUBLICATIONS

European Search Report completed Feb. 23, 2015 for corresponding Application No. EP14190346.

*Primary Examiner* — Michael Rozanski
(74) *Attorney, Agent, or Firm* — Louis J. Capezzuto

(57) ABSTRACT

An apparatus, including a bus having electrical power and data lines, and a plurality of location pads, which are positionable at different, respective locations with respect to a body cavity in which the object is located, and which are connected to the bus in series so as to receive electrical power and exchange data signals over the bus. Each location pad includes multiple radiator coils and driving circuitry configured to select, responsively to the data signals, different respective driving frequencies for the coils and to generate, using the electrical power from the bus, driving signals to drive the coils to produce magnetic fields at the respective driving frequencies. The apparatus also includes a console, which is configured to receive and process sensor signals from a magnetic sensor fixed to the object, in response to the magnetic fields in the body cavity, in order to compute position coordinates of the object.

19 Claims, 4 Drawing Sheets

SERIALLY CONNECTED AUTONOMOUS LOCATION PADS

FIELD OF THE INVENTION

The present invention relates generally to medical imaging, and specifically to using serially connected location pads to track a location of an object inserted into a body cavity of a patient.

BACKGROUND OF THE INVENTION

A wide range of medical procedures involve placing objects, such as sensors, tubes, catheters, dispensing devices and implants, within a patient's body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

There is provided, in accordance with an embodiment of the present invention, an apparatus for tracking an object, including, a bus including electrical power and data lines, a plurality of location pads, which are positionable at different, respective locations with respect to a body cavity in which the object is located, and which are connected to the bus in series so as to receive electrical power and exchange data signals over the bus, each location pad including multiple radiator coils, and driving circuitry, which is configured, responsively to the data signals, to select different respective driving frequencies for the radiator coils in the location pad and to generate, using the electrical power from the bus, driving signals to drive the coils to produce magnetic fields at the respective driving frequencies, and a console, which is configured to receive and process sensor signals from a magnetic sensor fixed to the object, in response to the magnetic fields in the body cavity, in order to compute position coordinates of the object.

In some embodiments, the body cavity may include a chamber of a heart, and the object may include an intracardiac catheter. In additional embodiments, first given radiator coils on a first given location pad may have a first operating volume, second given radiator coils on a second given location pad adjacent to the first given location pad may have a second operating volume, and the second operating volume may overlap the first operating volume.

In further embodiments, the respective driving frequencies of the first given radiator coils may differ from the respective driving frequencies of the second given radiator coils. In supplementary embodiments, the multiple radiator coils may include three sets of three radiator coils, and the three radiator coils can be arranged in an orthogonal configuration. In additional embodiments, a given driving circuitry can be configured to switch the electrical power to its respective radiator coils in response to computing a location corresponding to the position coordinates, the respective radiator coils having an operating volume.

In embodiments where the given driving circuitry can be configured to switch the electrical power to its respective radiator coils in response to computing a location corresponding to the position coordinates, the given driving circuitry can be configured to switch the electrical power by conveying the electrical power from the bus to its respective radiator coils upon the operating volume including the location. In additional embodiments where the given driving circuitry can be configured to switch the electrical power to its respective radiator coils in response to computing a location corresponding to the position coordinates, the given driving circuitry can be configured to switch the electrical power by switching off the electrical power to the respective radiator coils upon the respective operating volume not including the location.

In some embodiments, switching off the electrical power can be selected from a list including reducing the electrical power conveyed from the serial bus to the respective radiator coils, and ceasing to convey the electrical power from the serial bus to the respective radiator coils.

There is also provided, in accordance with an embodiment of the present invention, a method for tracking an object, the method including positioning a plurality of location pads at different, respective locations with respect to a body cavity, the location pads being connected in series to a bus so as to receive electrical power and exchange data signals over the bus, each location pad having respective driving circuitry and respective multiple radiator coils, selecting, by the driving circuitry on each of the location pads, different respective driving frequencies for the respective radiator coils in response to the data signals, using, by the driving circuitry on each of the location pads, the electrical power from the bus to generate driving signals to drive the respective radiator coils to produce magnetic fields at the respective driving frequencies, and upon inserting the object into the body cavity, receiving, by a console processor, signals from a magnetic sensor fixed to the object in response to the magnetic fields in the body cavity, and processing the received signals to compute position coordinates of the object.

There is further provided, in accordance with an embodiment of the present invention, a computer software product operated in conjunction with a plurality of location pads positioned at different, respective locations with respect to a body cavity of a patient, the location pads being connected to a bus in series so as to receive electrical power and exchange data signals over the bus, each location pad having respective driving circuitry and respective multiple radiator coils, and an object that is configured for insertion into the body cavity and includes a magnetic sensor for measuring a location of a distal end of the object, the product including a first non-transitory computer-readable medium, in which first program instructions are stored, which instructions, when read by the driving circuitry on each of the location pads, cause the driving circuitry on each of the location pads to select different respective driving frequencies for the respective radiator coils in response to the data signals, and to generate, using the electrical power from the bus, driving signals to drive the coils to produce magnetic fields at the respective driving frequencies, and a second non-transitory computer-readable medium, in which second program instructions are stored, which instructions, when read by a console processor, cause the console processor, to receive signals from the magnetic sensor in response to the magnetic fields in the body cavity, and to process the received signals to compute position coordinates of the object.

BRIEF DESCRIPTION OF THE DRAWINGS

The disclosure is herein described, by way of example only, with reference to the accompanying drawings, wherein.

DETAILED DESCRIPTION OF EMBODIMENTS

Overview

Embodiments of the present invention provide methods and systems for tracking an object (e.g., an intracardiac catheter) inserted into a body cavity (e.g., a chamber of a heart) of a patient during a medical procedure. In some embodiments, a plurality of location pads having respective driving circuitry and respective multiple coils can be connected in series to a bus so as to receive electrical power and exchange data signals over the bus, and be positioned at different respective locations with respect to the body cavity.

As explained hereinbelow, in response to the data signals received via the bus, a given location pad's respective driving circuitry can be configured to select different respective driving frequencies for its respective radiator coils, and to use the electrical power from the bus to generate driving signals to drive the respective radiator coils pad to produce magnetic fields at the respective driving frequencies. In operation, upon the object being inserted into the body cavity, a console coupled to the bus can receive, from a magnetic sensor fixed to the object, signals in response to the magnetic fields in the body cavity, and process the received signals to compute position coordinates that include a location of the object.

Additionally, a given pad's driving circuitry can be configured to switch the electrical power to its respective radiator coils in response to the computed location. In embodiments where the respective radiator coils of a given location pad have a specific operating volume, the given location pad's driving circuitry can convey the electrical power from the bus to the respective radiator coils upon the operating volume including the computed location, and can switch off (or reduce) the electrical power to the respective radiator coils upon the respective operating volume not including the computed location, thereby reducing power consumption.

System Description

Figure 1:
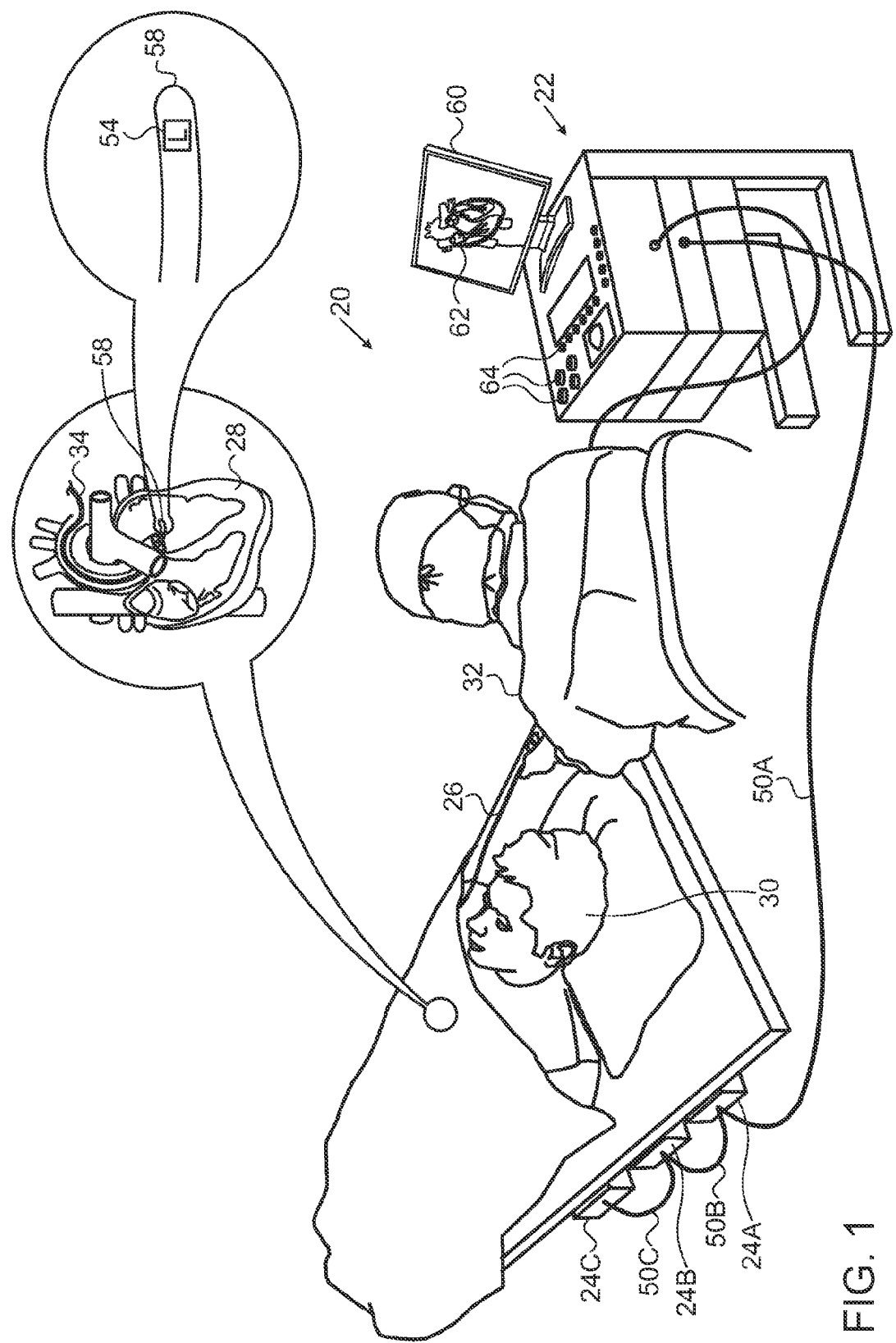
FIG. 1 is a schematic pictorial illustration of a medical system comprising a console and multiple serially connected location pads, in accordance with an embodiment of the present invention.
Figure 2:
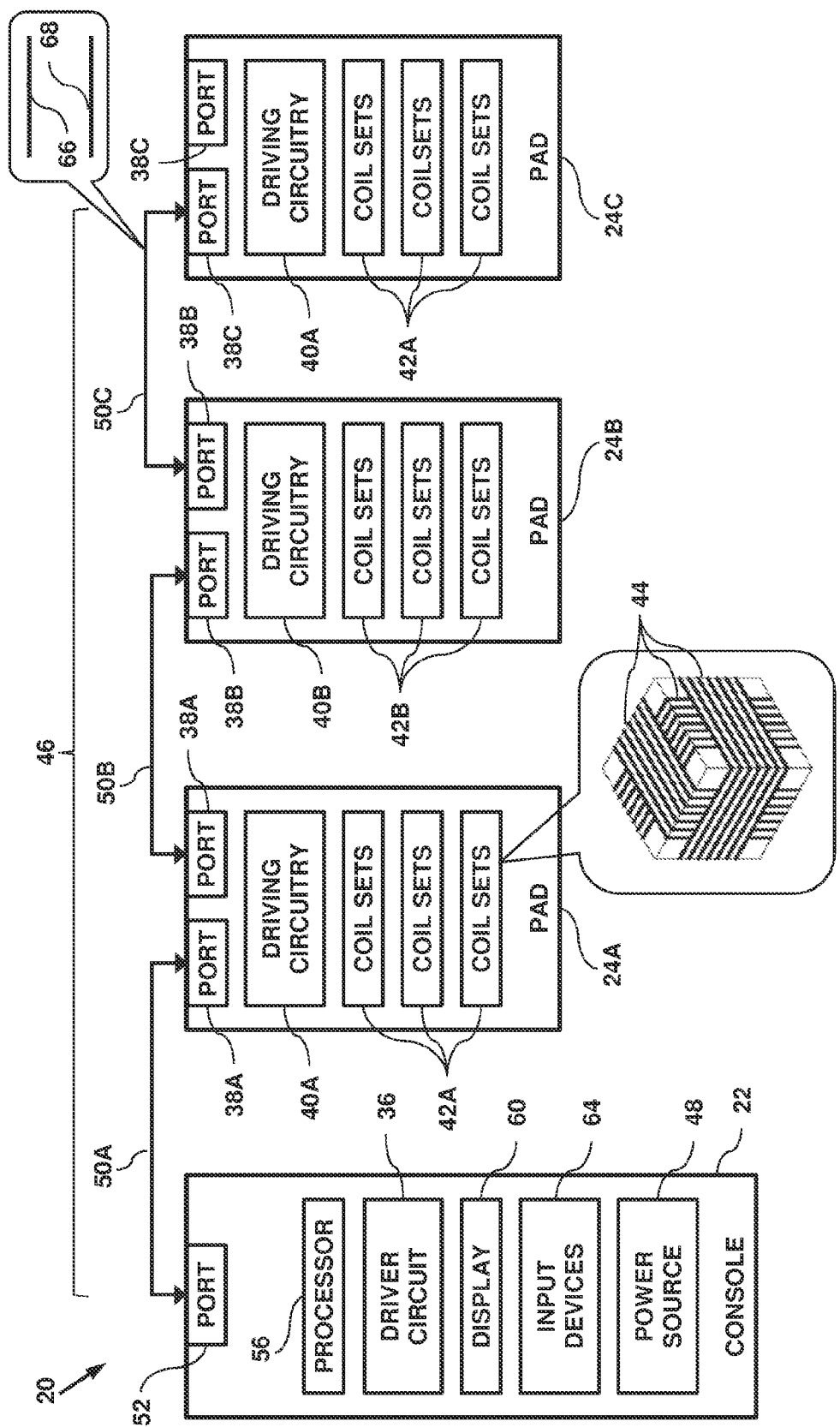
FIG. 2 is a block diagram of the console and the location pads, in accordance with an embodiment of the present invention.

FIG. 1 is a schematic, pictorial illustration of medical system 20 that comprises a control console 22 and multiple location pads 24, and FIG. 2 is a block diagram of the console and the location pads, in accordance with an embodiment of the present invention. System 20 comprises a probe 26, such as an intracardiac catheter that is used for diagnostic or therapeutic treatment, such as for mapping electrical potentials in a heart 28 of a patient 30. Alternatively, probe 26 may be used, mutatis mutandis, for other therapeutic and/or diagnostic purposes in the heart or in other body organs.

An operator 32 inserts probe 26 through the vascular system of patient 30 so that a distal end 34 of the probe enters a chamber of heart 28. Console 22 typically uses magnetic position sensing to determine position coordinates of distal end 34 inside heart 28. To determine the position coordinates, a driver circuit 36 in console 22 drives location pads 24 to generate magnetic fields within the body of patient 30.

In the example shown in FIG. 1 (and FIG. 3 hereinbelow), location pads 24 are placed below the patient's torso at known locations external to patient 30, and may be differentiated by appending a letter to the identifying numeral, so that the location pads comprise location pads 24A, 24B and 24C. Location pads 24 comprise two pad ports 38, pad driver circuitry 40 and multiple coils sets 42. In the example shown in FIG. 2, each pad 24 comprises three coil sets 42, and each of the coil sets comprises three radiator coils 44 arranged in an orthogonal configuration, thereby totaling nine radiator coils 44 on each pad 24.

A serial bus 46 conveys electrical power (also referred to herein as power) received from a power source 48 in console 22, and conveys data signals between console 22 and location pads 24. In the configuration shown in FIG. 2, serial bus 46 comprises multiple serial connections 50, with each of the serial connections typically comprising a cable comprising one or more data lines 66 configured to convey data signals and one or more power lines 68 configured to convey electrical power. Serial connections 50 may be differentiated by appending a letter to the identifying numeral, so that the serial connections comprise a serial connection 50A that couples console 22 and pad 24A, a serial connection 50B that couples pad 24A and pad 24B, and a serial connection 50C that couples pad 24B and pad 24C.

Console 22 comprises a console port 52 that enables the console to interact with probe 26, to convey the electrical power from power source 48 to serial bus 46, and to communicate with the location pads. To convey electrical power to pads 24 in the daisy-chain configuration shown in FIG. 2, console port 52 conveys the electrical power from power source 48 to pads 24 via serial connections 50A, 50B and 50C. In operation, a given pad 24 receives the electrical power from a first serial connection 50 via a first pad port 38, uses some of the electrical power to power components on the given pad, and conveys the remaining electrical power to a second serial connection 50 via a second pad port 38.

Pads 24 communicate with each other and console 22 in a similar manner, except that data signals can be conveyed in two directions (as opposed to the electrical power that is conveyed in a single direction). For example, when console 22 sends a first data signal to pad 24B, the signal is conveyed via serial connections 50A and 50B, and pad 24B can send a second data signal to the console via serial connections 50B and 50A.

The daisy-chain configuration described herein can substantially reduce the wiring complexity associated with the use of multiple location pads 24. Additionally, the serial bus is easily scalable, since adding an additional pad requires only one cable that connects it to the previous "last" location pad. In some embodiments, within overall constraints set by console processor 56, each pad 24 can be configured, using its respective driving circuitry 40, to operate autonomously. As explained hereinbelow, each pad can select each of the nine frequencies at which its respective coils radiate electromagnetic fields, and switch electrical power (received from console 22 via the serial connection) on and off to these coils.

Coil sets 42 generate magnetic fields in a predefined working volume that contains heart 28. A magnetic field sensor 54 (also referred to herein as magnetic sensor 54) within distal end 34 of probe 26 generates electrical signals in response to these magnetic fields. A console processor 56 processes these signals in order to determine the position coordinates of a distal tip 58 of probe 26, typically including both location and orientation coordinates. The method of position sensing described hereinabove is implemented in the CARTO™ system produced by Biosense Webster of Diamond Bar, Calif., and is described in detail in the patents and patent applications cited above.

Magnetic sensor 54 transmits a signal to console 22 that is indicative of the position coordinates of distal tip 58. Magnetic sensor 54 may comprise one or more probe coils (not shown), and typically comprises multiple probe coils oriented along different axes. Typically, sensor 54 comprises three probe coils arranged orthogonally. Although FIG. 1 shows a probe with a single magnetic sensor, embodiments of the present invention may utilize probes with more than one magnetic sensor. Magnetic position tracking techniques are described, for example, in U.S. Pat. Nos. 5,443,489, 6,788, 967, 6,690,963, 5,558,091, 6,172,499, and 6,177,792, whose disclosures are incorporated herein by reference.

Based on the signals received from probe 26 (via console port 52 and other components of system 20), processor 56 drives a display 60 to present operator 32 with an image 62 showing the location of distal end 34 in the patient's body, as well as status information and guidance regarding the procedure that is in progress. In some embodiments, operator 32 can manipulate image 62 using one or more input devices 64.

Driving circuitries 40 and processor 56 typically comprise general-purpose computers, with suitable front end and interface circuits for receiving signals from probe 26 and controlling the other components of console 22. Driving circuitries 40 and processor 56 may be programmed in software to carry out the functions that are described herein. The software may be downloaded to console 22 and location pads 24 in electronic form, over a network, for example, or it may be provided on non-transitory tangible media, such as optical, magnetic or electronic memory media. Alternatively, some or all of the functions of driving circuitries 40 and processor 56 may be carried out by dedicated or programmable digital hardware components.

Location Pads with Overlapping Magnetic Fields

Figure 3:
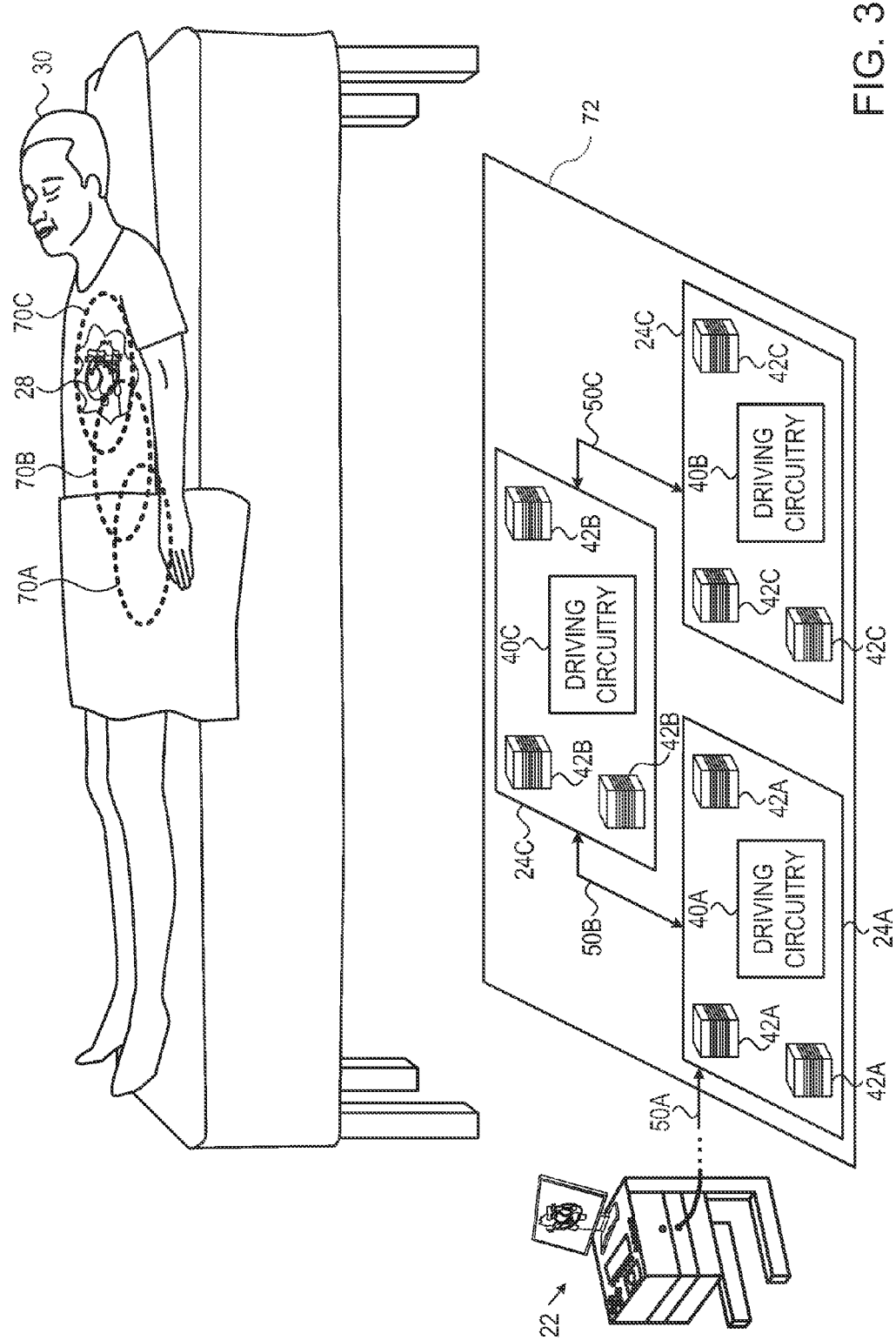
FIG. 3 is a schematic pictorial illustration of the location pads positioned under a patient during a medical procedure, in accordance with an embodiment of the present invention.

FIG. 3 is a schematic pictorial illustration of pads 24 positioned under patient 30 during a medical procedure, in accordance with an embodiment of the present invention. In embodiments of the present invention each pad 24 has a relatively small corresponding operating volume 70 within which processor 56 can track objects such as distal end 34 of probe 22. Operating volumes 70 may be differentiated by appending a letter to the identifying numeral, so that the operating volumes comprise operating volumes 70A, 70B and 70C. In the description herein, operating volume 70A comprises the corresponding operating volume for location pad 24A, operating volume 70B comprises the corresponding operating volume for location pad 24B, and operating volume 70C comprises the corresponding operating volume for location pad 24C.

As shown in FIG. 3, the location pads can be fixedly mounted on a board 72 so that operating volumes 70A, 70B and 70C overlap in order to create a contiguous operating volume 70 where processor 56 can track locations of distal tip 58 as operator 32 maneuvers probe 26 during a medical procedure. While the configuration in FIGS. 1-3 figure show three pads 24A, 24B and 24C having respective operating volumes 70A, 70B and 70C, any number of location pads 24 (and corresponding operating volumes 70) coupled via serial bus 46 are considered to be within the spirit and scope of the present invention.

In configurations where a first location pad 24 has a first operating volume 70 and a second location pad 24 has a second operating volume 70, the driving circuitries of the first and the second location pads can be configured to select the respective driving frequencies so that the driving frequencies of the coils on the first location pad are different from the driving frequencies of the second location pad, thereby enabling processor 56 to accurately detect locations of distal tip 58 as the operator maneuvers the distal tip between the first and the second operating volumes.

Figure 4:
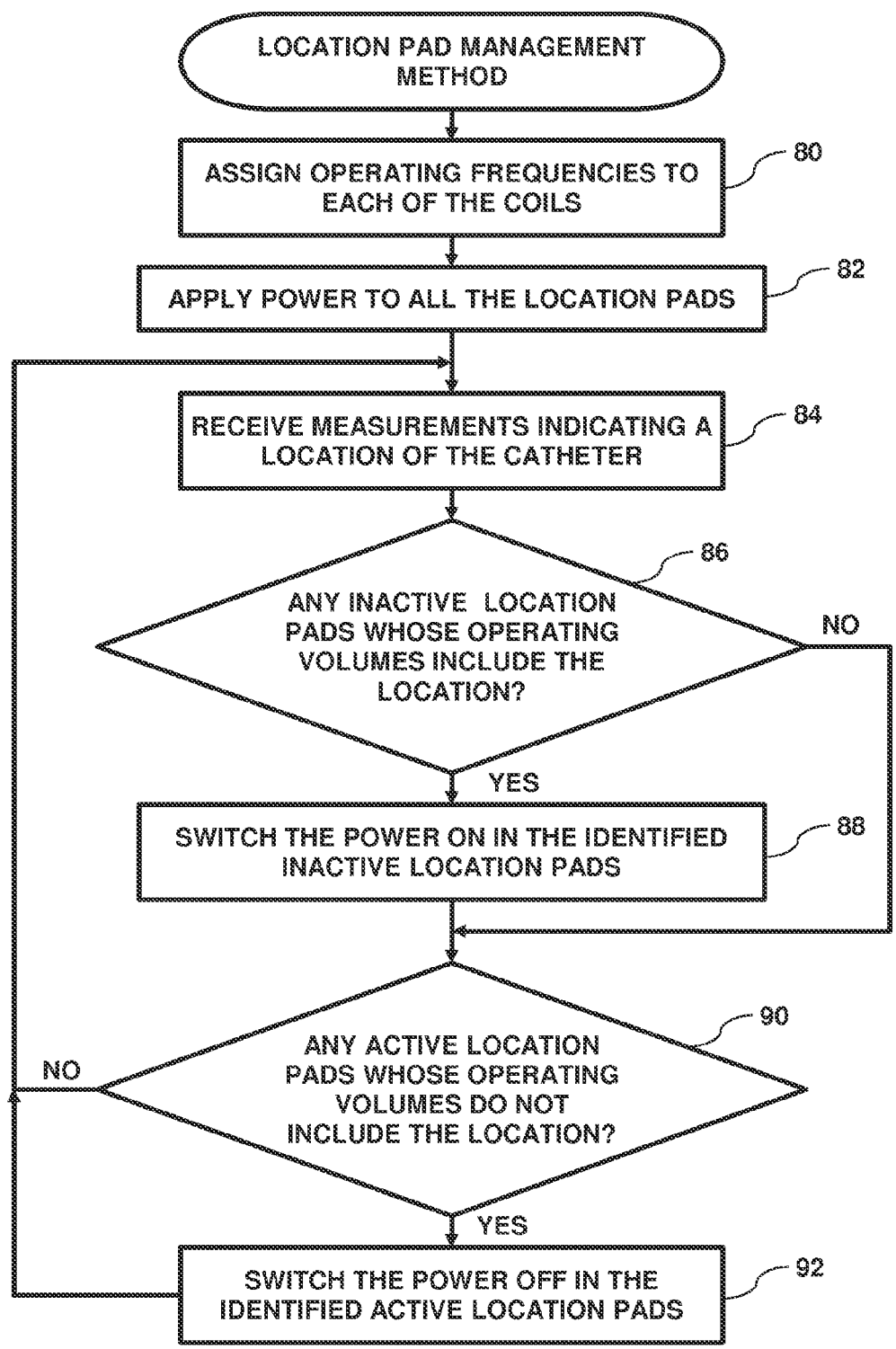
FIG. 4 is a flow diagram that schematically illustrates a method of managing the location pads during the medical procedure, in accordance with an embodiment of the present invention.

FIG. 4 is a flow diagram that schematically illustrates a method of managing location pads 24, in accordance with an embodiment of the present invention. In a configuration step 80, console processor 56 conveys a configuration message to each driving circuitry 40 in system 20, and upon receiving the configuration message, each of the driving circuitries assigns respective operating frequencies to its respective coils 44.

To configure a given pad 24, the given pad's driving circuitry 40 assigns a distinct frequency to each of the given pad's nine coils 44 (each pad 24 comprises three coil sets 42 that comprise three coils 44). Additionally, as described supra, in configurations comprising overlapping volumes 70, a given driving circuitry 40 of a given pad 24 can communicate with any adjacent pads 24 having overlapping volumes 70 in order to configure coils 44 so that each coil on the given pad and the adjacent pad(s) transmits at a distinct frequency.

In the configuration shown in FIG. 3, driving circuitry 40B communicates with driving circuitries 40A and 40C to ensure that each coil 44 on location pads 24A, 24B and 24C transmits at distinct frequencies. FIG. 3 presents the frequency distribution as a Venn diagram, wherein operating volume 70A indicates a first set of nine frequencies used by coils 44A, operating volume 70B indicates a second set of nine distinct frequencies used by coils 44B, and operating volume 70C indicates a third set of nine distinct frequencies used by coils 44C. Since the second set of nine frequencies has a first intersection with the first set of nine frequencies and a second intersection with the third set of nine frequencies, driving circuitries 40A, 40B and 40C need to select a distinct frequency for each of the 27 coils on the three location pads in system 20.

In an initialization step 82, processor 56 conveys a pad activation message to one or more driving circuitries 40 to switch on all coils 44 on the one or more location pads. As described hereinbelow, system 20 is configured to switch power on and off to respective coils 44 of a given pad 24 based on a current location of distal tip 58. In the description herein, an active pad 24 comprises a given location pad presently conveying full power to its respective coils 44 in order to generate magnetic fields, and an inactive pad 24 comprises a given location pad that is presently not conveying any power to its respective coils 44 (or is presently conveying reduced power to its respective coils). Therefore, at any time during a medical procedure using probe 26, each pad 24 is either active or inactive.

In a first embodiment, processor 56 can send the pad activation messages to all driving circuitries 40, and all the processors can fully power coils 44 from electrical power carried on serial bus 46. In a second embodiment, operator 32 can select, using input devices 64, a given pad 24 whose respective operating volume 70 includes a location of distal tip 58 at the beginning of a medical procedure. Upon detecting the selection, processor 56 can convey a pad activation message to the respective driving circuitry 40 of the given pad, and upon receiving the power initialization message, the respective driving circuitry can fully power the coils on the given pad.

In some embodiments, system 20 may use the fixed positioning of pads 24 on board 72 to register and delineate volumes 70. Alternatively or additionally, in a calibration phase of initialization step 82, sensor 54 may be moved to known locations with respect to board 72, and signals from the sensor may be used to register and delineate the volumes.

In a receive step 84, processor 56 receives measurements from magnetic sensor 54 indicating a location of distal tip 58 in patient 30. In embodiments of the present invention, the measurements include values of the respective frequencies of coils whose operating volume 70 includes the location of distal tip 58.

In a first comparison step 86, if there are any inactive location pads 24 whose respective operating volumes 70 include the location of distal tip 58, then in a first power switch step 88, the inactive location pads identified in step 86 switch on power to their respective coils sets 42, thereby activating the pads identified in step 86. When power is switched on, sufficient electrical power is conveyed from the serial bus to the coils so that the coils can radiate their respective magnetic fields.

For example, initially pad 24A is active, pads 24B and 24C are inactive, and distal tip 58 is in a first location that is exclusively in volume 70A. As operator 32 maneuvers probe 26 so that distal tip 58 is in a second location shared by volumes 70A and 70B (i.e., the second location is in an intersection of volumes 70A and 70B), then driving circuitry 40B conveys power from serial connection 50B to coils sets 42B. In some embodiments, upon processor 56 identifying distal tip 58 moving from the first location to the second location, processor 56 can send a pad activation message to driving circuitry 40B, and driving circuitry 40B conveys power to coil sets 42B responsively to the pad activation message. In an alternative embodiment, processor 56 conveys real-time locations of distal tip 58 to driving circuitries 40, and driving circuitry 40B conveys power to coil sets 42B upon receiving the second location and identifying that the received second location is within its respective operating volume 70.

In a second comparison step 90, if there are any active location pads 24 whose respective operating volumes 70 do not include the location of distal tip 58, then in a second power switch step 92, the active location pads identified in step 90 switch off power to their respective coil sets 42 thereby inactivating the pads identified in step 90, and the method continues with step 84. In embodiments of the present invention, switching off the power may comprise either reducing the power conveyed from serial bus 46 (serial connection 50B in the present example) to coils 44B or ceasing all power to coils 44B. Continuing the example described supra, pads 24A and 24B are active, pad 24C is inactive, and distal tip 58 is located at the second location. As operator 32 maneuvers probe 26 so that distal tip 58 is at a third location that is exclusively in volume 70B, then driving circuitry 40A switches off the power to the coils in coil sets 42B.

In some embodiments, upon processor 56 identifying distal tip 58 moving from the second location to the third location, the console processor can send a pad deactivation message to driving circuitry 40A, and in response to the pad deactivation message, processor 40A deactivates coil sets 42A by switching of the coils in coil sets 42A, thereby placing coil sets 42A in a "standby" mode. In an alternative embodiment, processor 56 conveys real-time locations of distal tip 58 to driving circuitries 40, and driving circuitry 40A deactivates coil sets 42B upon receiving the third location and identifying that the received third location is not within its respective operating volume 70.

Returning to step 90, if there are no active location pads 24 whose respective operating volumes 70 do not include the location of distal tip 58, then the method continues with step 84. Returning to step 86, if there are no inactive location pads 24 whose respective operating volumes 70 include the location of distal tip 58, then the method continues with step 90.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An apparatus for tracking an object, comprising:
a bus comprising electrical power and data lines;
a plurality of location pads, which are configured to be positionable at different, respective locations with respect to a body cavity in which the object is located, and which are connected to the bus in series so as to receive electrical power and exchange data signals over the bus, each location pad comprising:
multiple radiator coils; and
driving circuitry comprising programmed software in each of the plurality of location pads, which is configured, responsively to the data signals, to select different respective driving frequencies for the radiator coils in the location pad and to generate, using the electrical power from the bus, driving signals to drive the coils to produce magnetic fields at the respective driving frequencies; and
a console, which is configured to receive and process sensor signals from a magnetic sensor fixed to the object, in response to the magnetic fields in the body cavity, in order to compute position coordinates of the object.

2. The apparatus according to claim 1, wherein the body cavity comprises a chamber of a heart and wherein the object comprises an intracardiac catheter.

3. The apparatus according to claim 1, wherein first given radiator coils on a first given location pad have a first operating volume, and wherein second given radiator coils on a second given location pad adjacent to the first given location pad have a second operating volume, and wherein the second operating volume overlaps the first operating volume.

4. The apparatus according to claim 3, wherein the respective driving frequencies of the first given radiator coils differ from the respective driving frequencies of the second given radiator coils.

5. The apparatus according to claim 1, wherein the multiple radiator coils comprise three sets of three radiator coils, the three radiator coils being arranged in an orthogonal configuration.

6. The apparatus according to claim 1, wherein a given driving circuitry is configured to switch the electrical power to its respective radiator coils in response to computing a location corresponding to the position coordinates, and wherein the respective radiator coils have an operating volume.

7. The apparatus according to claim 6, wherein the given driving circuitry is configured to switch the electrical power by conveying the electrical power from the bus to its respective radiator coils upon the operating volume including the location.

8. The apparatus according to claim 6, wherein the given driving circuitry is configured to switch the electrical power by switching off the electrical power to the respective radiator coils upon the respective operating volume not including the location.

9. The apparatus according to claim 8, wherein switching off the electrical power is selected from a list comprising reducing the electrical power conveyed from the serial bus to the respective radiator coils, and ceasing to convey the electrical power from the serial bus to the respective radiator coils.

10. A method for tracking an object, comprising:
    positioning a plurality of location pads at different, respective locations with respect to a body cavity, the location pads being connected in series to a bus so as to receive electrical power and exchange data signals over the bus, each location pad having respective driving circuitry comprising programmed software in each of the plurality of location pads and respective multiple radiator coils;
    selecting, by the driving circuitry on each of the location pads, different respective driving frequencies for the respective radiator coils in response to the data signals;
    using, by the driving circuitry on each of the location pads, the electrical power from the bus to generate driving signals to drive the respective radiator coils to produce magnetic fields at the respective driving frequencies; and
    upon inserting the object into the body cavity:
        receiving, by a console processor, signals from a magnetic sensor fixed to the object in response to the magnetic fields in the body cavity; and
        processing the received signals to compute position coordinates of the object.

11. The method according to claim 10, wherein the body cavity comprises a chamber of a heart and wherein the object comprises an intracardiac catheter.

12. The method according to claim 10, wherein first given radiator coils on a first given location pad have a first operating volume, and wherein second given radiator coils on a second given location pad adjacent to the first given location pad have a second operating volume, and wherein the second operating volume overlaps the first operating volume.

13. The method according to claim 12, wherein the respective driving frequencies of the first given radiator coils differ from the respective driving frequencies of the second given radiator coils.

14. The method according to claim 10, wherein the multiple radiator coils comprise three sets of three radiator coils, the three radiator coils being arranged in an orthogonal configuration.

15. The method according to claim 10, and comprising switching, by a given driving circuitry, the electrical power to its respective radiator coils in response to computing a location corresponding to the position coordinates, and wherein the respective radiator coils have an operating volume.

16. The method according to claim 15, wherein switching the electrical power comprises conveying the electrical power from the bus to the respective radiator coils upon the operating volume including the location.

17. The method according to claim 15, wherein switching the electrical power comprises switching off the electrical power to the respective radiator coils upon the respective operating volume not including the location.

18. The method according to claim 17, wherein switching off the electrical power is selected from a list comprising reducing the electrical power conveyed from the serial bus to the respective radiator coils, and ceasing to convey the electrical power from the serial bus to the respective radiator coils.

19. A computer software product, operated in conjunction with:
    a plurality of location pads configured to be positioned at different, respective locations with respect to a body cavity of a patient, the location pads being connected to a bus in series so as to receive electrical power and exchange data signals over the bus, each location pad having respective driving circuitry and respective multiple radiator coils, and
    an object that is configured for insertion into the body cavity and includes a magnetic sensor for measuring a location of a distal end of the object,
    the product comprising:
        a first non-transitory computer-readable medium in each of the plurality of location pads, in which first program instructions are stored, which instructions, when read by the driving circuitry on each of the location pads, cause the driving circuitry on each of the location pads:
            to select different respective driving frequencies for the respective radiator coils in response to the data signals, and
            to generate, using the electrical power from the bus, driving signals to drive the coils to produce magnetic fields at the respective driving frequencies; and
        a second non-transitory computer-readable medium, in which second program instructions are stored, which instructions, when read by a console processor, cause the console processor:
            to receive signals from the magnetic sensor in response to the magnetic fields in the body cavity; and
            to process the received signals to compute position coordinates of the object.

* * * * *